(12) United States Patent
Dominick et al.

(10) Patent No.: US 9,398,079 B2
(45) Date of Patent: *Jul. 19, 2016

(54) OPTIMIZATION OF A SOFTWARE APPLICATION IMPLEMENTED ON A CLIENT-SERVER SYSTEM

(71) Applicant: Siemens Aktiengesellschaft, Munich (DE)

(72) Inventors: Lutz Dominick, Eggolsheim (DE); Karlheinz Dorn, Kalchreuth (DE); Vladyslav Ukis, Nuremberg (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/278,722

(22) Filed: May 15, 2014

(65) Prior Publication Data

US 2014/0250171 A1 Sep. 4, 2014

Related U.S. Application Data

(63) Continuation of application No. 13/401,072, filed on Feb. 21, 2012, now Pat. No. 8,825,751.

(30) Foreign Application Priority Data

Feb. 22, 2011 (EP) .................................... 11155405

(51) Int. Cl.
*G06F 15/173* (2006.01)
*H04L 29/08* (2006.01)
*G06F 19/00* (2011.01)
*H04L 12/26* (2006.01)
*H04L 12/911* (2013.01)
*H04W 24/02* (2009.01)

(52) U.S. Cl.
CPC ............ *H04L 67/10* (2013.01); *G06F 19/3406* (2013.01); *H04L 43/08* (2013.01); *H04L 47/823* (2013.01); *H04L 67/34* (2013.01); *H04W 24/02* (2013.01)

(58) Field of Classification Search
None
See application file for complete search history.

(56) References Cited

U.S. PATENT DOCUMENTS

| 6,023,692 A | 2/2000 | Nichols |
| 6,636,242 B2 | 10/2003 | Bowman-Amuah |
| 6,782,374 B2 | 8/2004 | Nichols |

(Continued)

OTHER PUBLICATIONS

Office Action for European Application No. EP 11155405.
European Priority Document for European Application No. EP 11155405.

*Primary Examiner* — Joseph E Avellino
*Assistant Examiner* — Phyllis A Book
(74) *Attorney, Agent, or Firm* — Harness, Dickey & Pierce, P.L.C.

(57) ABSTRACT

In at least one embodiment, data relating to the usage and the operating status of a frontend module of a software application implemented on the client side is acquired continuously during the execution of the application by way of a monitoring frontend module implemented on the client side of a client/server system. This acquired usage and status data is transmitted by the monitoring frontend module to a monitoring backend module implemented on the server side. The usage and status data is stored by the monitoring backend module in a database on the server side. The usage and status data stored in the database is automatically analyzed by way of an analysis module. In the process, default settings of the software application are automatically modified by way of the analysis module on the basis of the result of the analysis in order to improve the performance of the application.

17 Claims, 1 Drawing Sheet

(56) References Cited

U.S. PATENT DOCUMENTS

| | | | |
|---|---|---|---|
| 7,162,390 B2 * | 1/2007 | Jowett | G06F 11/3616 702/182 |
| 7,188,091 B2 | 3/2007 | Huelsman et al. | |
| 7,389,208 B1 | 6/2008 | Solinsky | |
| 7,519,564 B2 | 4/2009 | Horvitz | |
| 8,356,001 B2 * | 1/2013 | Collazo | G06F 21/577 706/14 |
| 8,584,098 B2 * | 11/2013 | Schmelter | G06F 11/3404 717/130 |
| 2002/0174293 A1 | 11/2002 | Fox et al. | |
| 2003/0090515 A1 * | 5/2003 | Chang | H04N 5/4401 715/745 |
| 2004/0153791 A1 * | 8/2004 | Arend | G06N 5/022 714/26 |
| 2004/0199482 A1 | 10/2004 | Wilson | |
| 2006/0167730 A1 * | 7/2006 | Calderone | G06Q 10/06 709/246 |
| 2008/0189400 A1 * | 8/2008 | Norrie | H04L 12/2602 709/223 |
| 2010/0153313 A1 | 6/2010 | Baldwin et al. | |
| 2010/0228843 A1 * | 9/2010 | Ok | H04L 12/66 709/223 |
| 2010/0333167 A1 | 12/2010 | Luo et al. | |
| 2011/0138366 A1 * | 6/2011 | Wintergerst | G06F 11/3409 717/130 |
| 2011/0172963 A1 | 7/2011 | Gu et al. | |
| 2012/0072576 A1 | 3/2012 | Yumerefendi et al. | |
| 2012/0089664 A1 | 4/2012 | Igelka | |

\* cited by examiner

OPTIMIZATION OF A SOFTWARE APPLICATION IMPLEMENTED ON A CLIENT-SERVER SYSTEM

PRIORITY STATEMENT

This application is a continuation application of U.S. application Ser. No. 13/401,072, filed Feb. 21, 2012, which claims priority under 35 U.S.C. §119 to European patent application number EP 11155405 filed Feb. 22, 2011, the entire contents of each of which are hereby incorporated herein by reference.

FIELD

At least one embodiment of the invention generally relates to a method for automatically optimizing a software application implemented on a client-server system. At least one embodiment of the invention further generally relates to a device for performing the method. The method and the associated device of at least one embodiment serve in particular for automatically optimizing a medical engineering software application for displaying and diagnosing digital medical image data.

BACKGROUND

Modern-day medical (software) applications, i.e. application programs, generally have a great number of functions which permit a user to display, process and diagnose medical image data. For each function, or at least for each related group of functions, a specific user interface (UI) is usually defined comprising associated control elements such as e.g. buttons, text fields, key and/or mouse combinations, layouts, etc. which are intended to enable the function or function group to be used in as optimal a manner as possible. In the course of establishing clinical findings it is mostly the case here that a plurality of functions or function groups will be used one after the other in order to lead the user, i.e. a physician making use of the application, to a diagnostic result. The "performance" of the application represents a measure of the quality of the user friendliness of the application, which performance in turn expresses itself in the number of medical image datasets which can be diagnosed by a user on the average per time unit by means of the application.

The performance of a medical engineering application is dependent in practice on a multiplicity of factors, inter alia also on the interaction of the (software) application with the hardware-related conditions of the client-server system on which the application is implemented, as well as on the preferred method of working and the know-how of the individual users working with the application.

Many of these factors accordingly depend on the specific operating conditions of a medical application at the particular site of deployment and a priori can consequently be predicted and taken into account only to a limited extent during the development of the application. The performance actually achieved during the operation of a medical application is therefore often comparatively far removed from the attainable optimum. In view of the complexity of a state-of-the-art medical application it is on the other hand frequently not possible or only possible to a limited extent to tailor such an application individually to the particular deployment conditions on the grounds of the additional time, cost and effort associated therewith.

SUMMARY

At least one embodiment of the invention discloses an effective and easily realizable method for improving or even optimizing an (in particular medical) software application implemented on a client-server system in terms of the performance achieved during the operation of the application. At least one embodiment of the invention discloses a device that is suitable for automatically performing the method.

With regard to at least one embodiment, the method is disclosed. With regard to at least one embodiment, the device that is suitable for performing the method is disclosed. Advantageous embodiments and developments of the invention are indicated by the dependent claims.

With regard to a software application that is to be improved or even optimized, a distinction is made between an application frontend module that is implemented on the or each client of the client-server system, and an application backend module that is implemented on one or more servers of the client-server system. The device according to at least one embodiment of the invention comprises a monitoring frontend module implemented on the client side and a monitoring backend module implemented on the server side.

According to at least one embodiment of the method, data relating to the usage and the operating status of the application frontend module is collected continuously therein by means of the monitoring frontend module during the execution of the application. This usage and status data is transmitted by the monitoring frontend module to the monitoring backend module, by which the usage and status data is stored in a (usage) database created on the server side.

BRIEF DESCRIPTION OF THE DRAWINGS

In the following detailed description, example embodiments not to be understood in a limiting sense together with their features and further advantages will be described with reference to the accompanying drawings in which.

The invention will now be explained in greater detail on the basis of different example embodiments described in conjunction with the drawings.

It should be noted that these FIGS. are intended to illustrate the general characteristics of methods, structure and/or materials utilized in certain example embodiments and to supplement the written description provided below. These drawings are not, however, to scale and may not precisely reflect the precise structural or performance characteristics of any given embodiment, and should not be interpreted as defining or limiting the range of values or properties encompassed by example embodiments. For example, the relative thicknesses and positioning of molecules, layers, regions and/or structural elements may be reduced or exaggerated for clarity. The use of similar or identical reference numbers in the various drawings is intended to indicate the presence of a similar or identical element or feature.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments.

The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks will be stored in a machine or computer readable medium such as a storage medium or non-transitory computer readable medium. A processor(s) will perform the necessary tasks.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the following description, illustrative embodiments may be described with reference to acts and symbolic representations of operations (e.g., in the form of flowcharts) that may be implemented as program modules or functional processes include routines, programs, objects, components, data structures, etc., that perform particular tasks or implement particular abstract data types and may be implemented using existing hardware at existing network elements. Such existing hardware may include one or more Central Processing Units (CPUs), digital signal processors (DSPs), application-specific-integrated-circuits, field programmable gate arrays (FPGAs) computers or the like.

Note also that the software implemented aspects of the example embodiments may be typically encoded on some form of program storage medium or implemented over some type of transmission medium. The program storage medium (e.g., non-transitory storage medium) may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The example embodiments not limited by these aspects of any given implementation.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The device according to at least one embodiment of the invention also includes an analysis module which is likewise implemented in particular on the server side. The usage and status data stored in the database is analyzed automatically by way of the analysis module, in the course of which process, according to at least one embodiment of the method, the analysis module automatically modifies default settings of the application on the basis of the result of the analysis in order to improve the performance of the application.

In this context the term "default settings" generally encompasses all data that has an effect on the mode of operation of the application, and that can be modified without the requirement to recompile the application. Here, the default settings include in particular configuration data that affects the functionality or the runtime behavior of the application, that determines the look-and-feel of a user interface of the application or that defines the source and destination paths in the file system of the client-server system. The default settings also include directories for templates and sample files that are accessed by the application.

In the case of an application for diagnosing digital medical image data the default settings include in particular what is termed a "layout repository", in which are stored what are termed layouts which can optionally be accessed by the user interface of the application. The term "layout" in this context refers to a dataset which specifies the number and arrangement of the images that are to be displayed on the user interface.

In addition the default settings of the medical application beneficially include an "application template repository" (App Template Repository) in which "application templates" (App Templates) are held in readiness for selection. In this case each application template defines a set of functions with which the application frontend module can be started on a client, in particular a number of plug-ins which it may be necessary to load in addition to the basic functions of the application, a selection of the control elements for the user interface and—insofar as these are graphical control elements—instructions specifying their arrangement on the user interface, etc.

In a beneficial embodiment, the default settings of the medical application furthermore include a "user settings repository" in which a "user profile", i.e. a set of individual user settings is stored for each client user. In this case each user profile includes in particular links to the layouts preferred by the user for specific application cases, links to the application templates available to the user, and also details concerning the identity of the respective user, in particular name, login identification and password.

In an example embodiment variant of the invention, the usage and status data acquired by the monitoring frontend module includes in particular details concerning
  the identity of a client user,
  the or each application invoked by the client user,
  the attributes of the application layout,
  the status of a user interface of the application, in particular details concerning an application template on which the user interface may be based,
  the data loaded by the application,
  the user commands directed to the application, and
  the start time of the interaction.

In an example variant of the invention the usage and status data stored in the usage database is automatically searched by the analysis module for recurring command sequences of a client user. According to the method a "usage scheme" associated with such a command sequence is generated in this case by the analysis module and stored in the default settings of the application.

By "command" in this context is understood any interaction that a client user engages in with the application. Formally, such a command can reside in particular in the clicking of a button or the selection of a menu item of a graphical user interface, in the marking of a surface area on the user interface or in the pressing of a specific key or key combination, and for example include the loading of specific data from a memory, the displaying of the loaded data in a specific area of a user interface, the application of specific functions of the application, in particular image processing algorithms, to the loaded data and/or the storing of the (possibly modified) data.

A "usage scheme" is generally understood to be a program which automatically executes the respective command sequence within the scope of the application. The "usage scheme" is in particular what is termed a "macro" or a "workflow".

If the analysis module recognizes for example that after a specific type of image dataset has been loaded a client user repeatedly applies an image synthesizing (volume rendering (VR)) algorithm or a maximum intensity projection (MIP) to the loaded image data, in the above-described embodiment variant of the method the analysis module automatically generates a usage scheme in the course of which the volume rendering algorithm or the maximum intensity projection is automatically performed as soon as the client user loads an image dataset of the corresponding type.

In principle it can be provided within the scope of at least one embodiment of the invention that the analysis module will already generate a corresponding usage scheme at the time of the first identified repetition of a command sequence. It is however preferable, in order to limit the number of generated usage schemes to a manageable size for a client user, to specify further limiting conditions to the analysis module for generating a usage scheme associated with a repetitive command sequence.

In a beneficial embodiment variant the analysis module accordingly generates a usage scheme only for a command sequence which is repeated in the stored usage and status data multiple times, for example more than ten times. Furthermore, the required number of repetitions of a command sequence can also be coupled to a time period, such that the analysis module for example generates a usage scheme only when a corresponding command sequence is repeated more than x times (x=3,4,5, . . . ) within a specific time period. In an additional or alternative embodiment it is provided as a further limiting condition that a usage scheme is generated only for command sequences which comprise a minimum number of n (where n=3,4,5, . . . ) commands.

In principle it can furthermore be provided within at least one embodiment of the scope of the invention that the analysis module stores the or each usage scheme in such a way that the usage scheme is executed without further action on the part of the client user as soon as the client user initiates the first command of the associated command sequence. It is, however, preferred within the framework of the or each usage scheme for a prompt to be generated in which the client user—at least when the usage scheme is executed for the first time—is requested to confirm or reject the automatic execution of the usage scheme.

The generated usage schemes can be stored globally by the analysis module, i.e. so that they are accessible to all clients and client users. In contrast hereto it is optionally provided that the usage schemes are determined and/or stored on a user-specific basis. In addition or alternatively hereto it is provided according to a development of at least one embodiment of the invention that the usage schemes are determined and stored on a segment-specific basis. In this case the analysis module determines at which segment of a user interface of the application the same command sequences are repeatedly performed and generates corresponding usage schemes which are applied exclusively to the associated segment. If the analysis module recognizes for example that a specific data processing algorithm is regularly applied by one or more client users to data of a specific segment, it generates a usage scheme which automatically applies said image processing algorithm to the data displayed in this associated segment.

A "segment" in this context generally denotes an area of a user interface which can be reversibly marked or activated by user interaction, wherein an activated or marked segment forms a foreground of the user interface. Within the framework of a graphical user interface such a segment can be embodied for example as a "window" or "tab". In the case of an application for diagnosing digital image data such a segment is formed in particular by means of a display field for a medical image dataset.

In a further advantageous embodiment variant of the invention it is provided that on the basis of the analysis of the stored usage and status data the analysis module identifies that segment of a user interface comprising a plurality of segments with which a client user will, with the highest probability, first interact after the starting of the application frontend module or when a workflow is performed by means of the application frontend module. According to the method the analysis module in this case modifies the default settings of the application such that the identified segment will automatically be placed in the foreground when the application frontend module is started or at the start of processing of the workflow.

The "foreground" denotes that part of a user interface with which the client user can directly interact. In contradistinction to the foreground of the user interface, parts of the user interface that cannot be influenced directly or are hidden, in particular inactive windows or hidden tabs, form a "background" of the user interface.

A multistep activity defined and implemented within the framework of the application is generally referred to by the term "workflow". In an application for diagnosing medical image data, the diagnosis of a mammography dataset or the diagnosis of an MR tomography dataset of the head can be implemented for example as workflows.

In a further advantageous embodiment variant of the invention it is provided that on the basis of the analysis of the stored usage and status data the analysis module determines the (actuation) frequency with which graphical control elements of a user interface of the application are actuated on each occasion. According to the method the analysis module in this case modifies the default settings of the application in accordance with the result of the analysis in such a way that the control elements are arranged on the user interface in an order that is dependent on the actuation frequency. In particular the control elements are beneficially arranged in the order of their actuation frequency, in the case of menu items of a typical "drop-down menu", for example, from top to bottom with decreasing actuation frequency, or in the case of a series of icons or buttons, for example, from left to right with decreasing actuation frequency. The advantage achieved by means of this method variant is that after the rearrangement frequently used control elements are more easily and more quickly accessible to the client user.

In a beneficial development of at least one embodiment of the invention the analysis module determines on the basis of the identified actuation frequency those control elements which are not or only rarely used by a client user. In this case the analysis module modifies the default settings of the application such that the unused or rarely used control elements and the associated program routines (tools) of the application are no longer loaded automatically at the time of a restart by the relevant client user, as a result of which the resource requirements of the application are reduced.

According to another advantageous variant of at least one embodiment of the invention it is provided that the analysis module determines the (access) frequency with which specific datasets are accessed by way of the application. In this case the analysis module allocates each of the checked datasets a storage location within the file system of the client-server system in accordance with the determined access frequency. In particular the analysis module arranges for datasets having high access frequency to be held available in a local memory or another memory having a short access time, while datasets having low access frequency by comparison are stored in an archive memory having a relatively long access time. The advantage achieved by means of this method variant is that frequently used datasets are available quickly for a client user, while on the other hand local memory areas are automatically cleared of datasets having low access frequency in order to counteract an overloading of these memory areas.

In a further advantageous variant of at least one embodiment of the invention the analysis module determines the (call) frequency with which the or each application is invoked. In this case, if the determined call frequency of an application exceeds a predefined threshold value, the analysis module modifies the default settings of said application in such a way that the associated application backend module is already started and operated independently of the or each frontend module of said application. In a refined embodiment of this variant of the invention the call frequency is in this case determined for the or each application in a time-resolved manner. The analysis module in this case determines in particular at which time of day a specific application is started particularly frequently by client users. In this case the analysis module starts the application backend module with a predefined lead time ahead of the determined peak times (i.e. the times of high call probability). The client-independent start of the application backend module has the advantage in this case that in the majority of cases said application backend module will already be running when a client user invokes the application on the client side. This has the advantage that in the perception of the client user the application "powers up" particularly quickly, in other words that the time interval between the calling of the application on the client side and the readiness of the application for productive work is particularly short.

In another variant of at least one embodiment of the invention it is provided that the analysis module determines the consumption of resources of the client-server system by the application. The analysis module in this case modifies the default settings of the application—in particular by corresponding configuration of an application starter—such that when the application is called by a client user it is only started if sufficient free resources are available on the client-server system. Alternatively it can be provided that if insufficient resources are available the application will be started with limited functionality only, and commensurately with reduced resource requirements.

In this connection the "resources" of the client-server system comprise in particular the available CPU power and the free working memory space as well as the free data transmission capacity of the required network and data bus components of the client-server system.

The advantage achieved by way of this variant of at least one embodiment of the invention is in particular that an overloading of the client-server system that would cause all of the already running applications and processes to slow down is avoided.

In order to impose the minimum possible load on the capacity of the client-server system due to the resource requirements of the analysis module it is preferably provided that the analysis module analyzes the usage and status data stored in the usage database discontinuously at regular time intervals, in particular once per day, and also makes the corresponding modifications to the default settings of the or each application discontinuously at corresponding time intervals. The analysis module is in this case active preferably at times of particularly low resource utilization, in particular during the night.

In an additional or alternative embodiment it is preferably provided likewise in order to disrupt the workflow of the or each application as little as possible that the or each application frontend module transmits the usage and status data collected by it to the monitoring backend module asynchronously, i.e. without blocking other processes, and hence in the background of the application.

In further variants of at least one embodiment of the invention the analysis module determines on the basis of the usage and status data changes which a client user makes to the layout or the status of a user interface of the application. In this case the analysis module produces new layouts or application templates which reflect the changes made by the client user. This variant of the invention has the advantage that the changes made by a client user to the layout or the status of the user interface can automatically be restored at a later time as well as made available to other client users.

Figure 1:
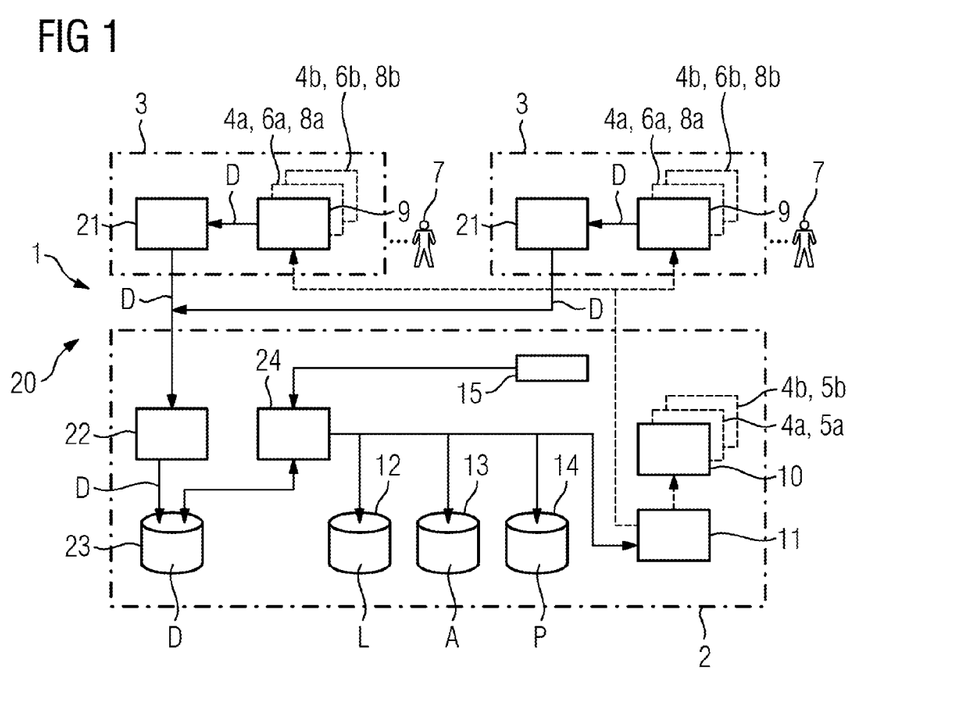
FIG. 1 is a schematic block diagram showing a client-server system having two medical engineering applications implemented thereon, and having a device for automatically optimizing said applications.

FIG. 1 is a rough schematic simplification showing a client-server system 1 which is deployed in a medical institution, for example a radiology department of a clinic. The client-server system 1 comprises a central server 2 and—in a simplified representation—two clients 3. The clients 3 are for example conventional desktop computers, in particular personal computers. For data transmission purposes the clients 3 are connected to the server 2 by way of a data communication network, a local area network (LAN) for example, that is not depicted in further detail.

Two medical (software) applications 4a and 4b are implemented by way of example on the client-server system 1. The application 4a is for example a program for displaying, processing and diagnosing CT image data (computer tomograms). The application 4b is for example a program for displaying, processing and diagnosing digital ultrasound images.

Each of the two applications 4a and 4b comprises an (application) backend module 5a and 5b, respectively, implemented on the server 2. Each of the two applications 4a and 4b also includes a number of (application) frontend modules 6a and 6b, respectively, of which one in each case is implemented on each of the two clients 3 for each application 4a and 4b. In this case the frontend modules 6a and 6b each contain at least part of what is termed the "presentation logic" of the respective application 4a and 4b, via which the applications 4a and 4b interact with a respective (client) user 7. For this purpose the frontend modules 6a and 6b each include in particular a graphical user interface 8a and 8b, respectively.

The application backend modules 5a and 5b contain at least the major part of what is called the "business logic", i.e. the actual utility routines for image and text processing as well as for medical diagnosis of the image data. However, the distribution (deployment) of the functionality of the individual applications 4a and 4b and the associated software layers over the server 2 and the clients 3 can be solved in different ways within the scope of the invention. According to the proportion of software layers arranged on the client side, the frontend modules 6a and 6b can be embodied here in particular as a so-called "fat client", "rich client", "smart client", "rich thin client" or "web client". The deployment of the application 4a can also be different in this case from the deployment of the application 4b.

The "lifecycle" of the applications 4a and 4b, i.e. the processes associated with the starting, termination and suspension of the respective application 4a and 4b, are controlled on the client side in each case by way of a (runtime control) frontend module 9 (App Frontend Runner) which is assigned to each of the two clients 3 and which starts, stops or suspends the respective frontend modules 6a, 6b of the applications 4a and 4b. The lifecycle of the application backend modules 5a and 5b is similarly controlled by a (runtime control) backend module 10 (App Backend Runner) implemented on the server side. The modules 9 and 10 are in turn jointly controlled by way of a software module referred to as an application starter 11, which is likewise implemented on the server side.

In order to determine the configuration—predefined on a client- and/or user-specific basis if necessary—of the applications 4a and 4b, the runtime control frontend modules 9 and the runtime control backend module 10 access a set of default settings which are assigned to the application 4a and 4b in each case. These default settings are stored in structured form in a (layout) directory 12, an (application templates) directory 13 and a (user settings) directory 14.

The layout directory 12 in this case contains a number of layouts L assigned by the respective application 4a or 4b, each of which predefines a number of segments for the user interface 8a or 8b of a client 3, as well as the size and arrangement of said segments. In this case each segment is a display field in which a medical image can be presented.

So-called application templates A are stored in the application templates directory 13 for each application 4a and 4b. In this case each application template A defines a set of functions for the associated application 4a or 4b. Within the framework of each individual application template A it is thus specified in particular which control elements are to be represented on the user interface 8a or 8b of the respective application 4a or 4b, and how these control elements are to be arranged.

For each client user 7, the user settings directory 14 includes a user profile P which inter alia contains details relating to the layouts L preferred by the individual client user 7 for specific application scenarios as well as to the application templates A that are available to the user 7. In this case the user profile P contains in particular pointers (links) to the corresponding layouts L in the layout directory 12 or application templates A in the application templates directory 13.

Also implemented on the server 2 is a (data) archiving module 15 which periodically carries out archiving of the image data held available in a local memory of the server 2 in an archive or long-term storage facility.

Additionally implemented on the client-server system 1 is a device 20 for optimizing the performance of the two applications 4a and 4b. This device 20 comprises a number of monitoring frontend modules 21, one of which is assigned to each one of the clients 3. The device 20 furthermore comprises a monitoring backend module 22 implemented on the server side, a usage database 23 and an analysis module 24.

The above-cited modules 5a,5b,6a,6b,9,10,11,12,13,14, 15,21,22, 23 and 24 are software modules.

Figure 2:
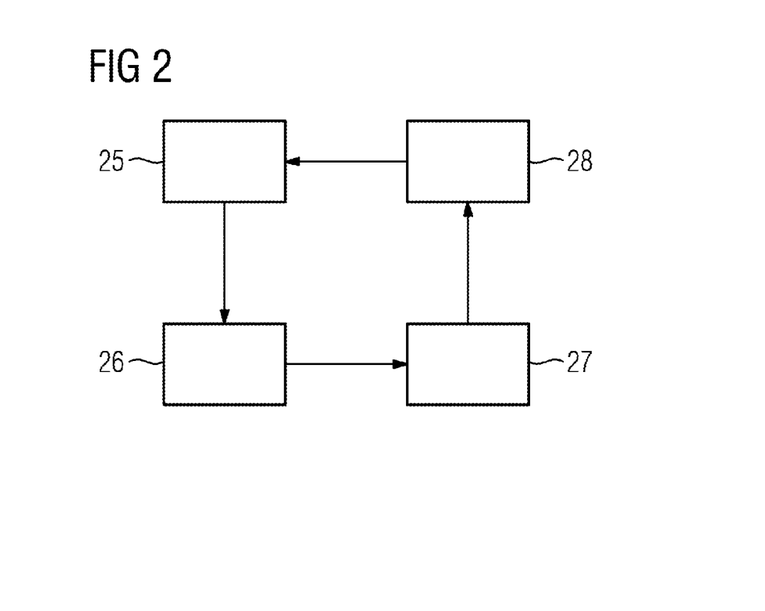
FIG. 2 is a schematic flow chart showing a method performed by the device according to FIG. 1 in order to improve or even optimize the applications.

According to FIG. 2, the starting point and precondition for the optimization method performed by way of the device 20 is the normal operation of the client-server system 1, in which at least one of the two applications 4a or 4b is used by at least one of the client users 7, such that at least one frontend module 6a,6b as well as the backend module 5a,5b of said application 4a,4b are running.

After the application 4a or 4b has been started (step 25 in FIG. 2) the monitoring frontend module 21 continuously collects data D relating to the usage and status of the or each application frontend module 6a,6b installed on said client 3 by interacting with the runtime control frontend module 9 of the respective client 3. Said (usage and status data) data D includes in particular details relating to the identity of the client user 7 working at the respective client 3 (and for that purpose "logged in"),
the applications 4a,4b running on the respective client 3,
the currently used layout L of the or each application 4a,4b,
the current status of the user interface 8a or 8b, in particular
  the status of the buttons, text fields, routines, as well as the presentation status of the user interface 8a,8b ("presentation status" in this context refers to the status of the user interface in which the client user 7 leaves behind a study; for example, the study is left in a layout comprising 16 images arranged in a 4×4 matrix, wherein the client user 7 has for example inserted two distance lines in a first image, and wherein the client user 7 has for example noted medical findings relating to the fifth and tenth image in each case),
the data loaded by the respective application 4a and 4b,
the operating mode of the respective application 4a,4b, assuming the application 4a,4b can be operated in a plurality of operating modes (in the case of the application 4a, for example, there is a choice between a 2D mode, a 3D mode and a volume rendering mode), and
the start time of the user interaction.

Each of the two monitoring frontend modules 21 sends the usage and status data D collected by it to the monitoring backend module 22 implemented on the server side. In this case the usage and status data D is transmitted asynchronously as a background process (background job) in order not to degrade the performance of the respective client 3. The collected usage and status data D sent to the server 2 is fed into the usage database 23 in structured form by the monitoring backend module 22. The collection of the usage and status data D, its transmission from the respective client 3 to the server 2 and the feeding of said data into the usage database 23 are indicated in summary form in FIG. 2 by step 26.

In a following step 27 the analysis module 24 analyzes the usage and status data D in the usage database 23 for the occurrence of predefined patterns and if such patterns are detected modifies the default settings of the respectively associated application 4a or 4b in a predefined case-specific manner in each instance in order to improve the performance of the application 4a or 4b. For this the analysis module 24 uses in particular the analysis schemes listed in the left-hand column in TAB 1 and makes the changes listed in the center column in each case to the default settings of the application 4a,4b in accordance with the respective analysis result (step 28). The effect of the respective change for the client user 7 is indicated in the right-hand column in Table 1.

TABLE 1

| Analysis scheme | Change | Effect of the change |
| --- | --- | --- |
| The client user 7 modifies a predefined layout L | The analysis module 24 adds the modified layout L to the layout directory 12 | The modified layout L is displayed directly at the time the respective application 4a, 4b is started, with no need for it to be restored manually |
| After specific data has been loaded, the client user 7 regularly interacts first with a specific segment of the user interface 8a, 8b | The analysis module 24 modifies the current application template A in such a way that the identified segment with which the client user 7 will, with the highest probability, first interact, is automatically placed in the foreground of the user interface 8a, 8b after such data has been loaded | In the majority of cases the focus is placed directly on the desired segment, with no need to click on the segment or for any other user action |
| The user 7 regularly executes specific commands in specific segments of the user interface 8a, 8b having specific loaded data (for example he/she applies specific image processing algorithms such as VR or MIP in specific segments) | The analysis module 24 sets corresponding layouts L and user settings in the directories 12 and/or 14 | In the identified segments the determined user commands, in particular the application of VR or MIP, are executed automatically, with no need for the client user 7 to invoke said functionality manually |
| The user modifies the configuration of a specific functionality of an application 4a, 4b | The analysis module sets corresponding user settings in the directory 14 | The configuration change is automatically completed at a restart of the |

TABLE 1-continued

| Analysis scheme | Change | Effect of the change |
|---|---|---|
| (for example he/she makes a specific selection in the volume rendering gallery) | | application 4a, 4b, so the change does not have to be repeated manually |
| The user 7 applies specific settings in a specific application 4a, 4b | The analysis module 24 sets corresponding user settings in the directory 14 | At the restart the application 4a, 4b is automatically loaded with the new settings |
| The user generates a special workflow in order to process the latter with one of the applications 4a, 4b | The analysis module 24 implements the new workflow in the associated application template A | The workflow is generated automatically at a restart of the application 4a, 4b |
| The client user 7 actuates specific menu items particularly frequently | The analysis module 24 modifies the associated application template A of the respective application 4a, 4b such that frequently actuated menu items are arranged above less frequently actuated menu items | The client user 7 can access frequently used menu items more easily and more quickly |
| The client user 7 accesses specific datasets particularly frequently | The analysis module 24 configures the archiving module 15 in such a way that data is archived if its access frequency falls below a threshold value, or stored in the local memory if its access frequency exceeds the threshold value | The user 7 can access frequently needed data comparatively quickly; at the same time the local memory of the server 2 is cleared of rarely needed data |
| One of the applications 4a and 4b is invoked with particular frequency on the clients 3 at a specific time of day | The analysis module 24 configures the application starter 11 in such a way that the backend module 5a, 5b of said application 4a, 4b is pre-started with a specific lead time ahead of said time of day | From the perspective of the client user 7 the corresponding application 4a, 4b powers up faster, since only the associated frontend module 6a, 6b still needs to be started when the application 4a, 4b is invoked |
| The analysis module 24 empirically determines the resource consumption of the application 4a, 4b | The analysis module 24 configures the application starter 11 in such a way that when invoked by a client user 7 the respective application 4a, 4b will only be started if sufficient free resources of the client-server system 1 are available | An overloading of the client-server system 1 is avoided, with the result that the vast majority of processes run at a satisfactory speed |
| A client user 7 does not or only rarely actuates specific control elements of the user interface 8a, 8b | The analysis module 24 modifies the associated application template A - optionally on a data-type-specific or user-specific basis - such that the unused or rarely used control elements and the associated program routines of the application 4a, 4b are no longer loaded | The resource consumption of the application 4a, 4b and the clarity of the associated user interface 8a, 8b are improved |
| | | automatically at the start of the application |

The analysis module 24 in this case performs the analysis and the associated modification of the default settings of the respective application 4a, 4b discontinuously at 24-hour intervals, specifically during the night.

The automatic modification of the default settings of the respective application 4a, 4b results in the creation of a feedback process in the course of which the respective application 4a is started at the time of each daily restart with new default settings that have been improved in terms of application performance (see FIG. 2). Accordingly, the applications 4a and 4b are constantly optimized in respect of their performance.

In an example embodiment, it is provided that the described optimization process can be switched on and off on a user-specific basis. In particular it is provided that in the case of particularly performance-critical applications, such as applications 4a,4b deployed to track operations for example, the acquisition of usage and status data D is deactivated by the monitoring frontend module 21.

The user-specifically optimized default settings of the applications 4a,4b can optionally be made accessible to all users 7 and/or also be reused for the client-server systems 1 of other medical institutions.

The scope of the invention requiring protection is not, however, limited to the above-described example embodiment. Rather, numerous variants and developments of the described method can be discovered by the person skilled in the art within the spirit and scope of the invention.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

LIST OF REFERENCE SIGNS

1 Client-server system
2 Server
3 Client
4a,b (Software) application
5a,b (Application) backend module
6a,b (Application) frontend module
7 (Client) user
8a,b User interface
9 (Runtime control) frontend module
10 (Runtime control) backend module
11 Application starter
12 (Layout) directory
13 (Application templates) directory
14 (User settings) directory
15 (Data archiving) module
20 Device
21 (Monitoring) frontend module
22 (Monitoring) backend module
23 (Usage) database
24 Analysis module
25 Step
26 Step
27 Step
28 Step
A Application template
D (Usage and status) data
L Layout
P User profile

What is claimed is:

1. A method for automatically improving performance of a software application implemented on a client-server system, the method comprising:
  continuously acquiring data, during the execution of the application, the data related to the usage and the operating status of a frontend module of the application implemented on the client side, the data being acquired by way of a monitoring frontend module implemented on the client side;
  transmitting the acquired usage and status data, via the monitoring frontend module to a monitoring backend module implemented on the server side;
  storing the usage and status data, via the monitoring backend module, in a database on the server side;
  automatically analyzing, via an analysis module, the usage and status data stored in the database;
  identifying, via the analysis module, that segment of a user interface including a plurality of segments with which a client user will first interact via the client side after starting the application frontend module based on the analysis of the stored usage and status data; and
  automatically modifying, via the analysis module, default settings of the software application on the basis of a result of the analysis in order to improve performance of the application, the default settings indicating the segment of the user interface that are frequently first used by the user after starting the application such that the identified segment is automatically placed in a foreground of the user interface when the application frontend module is started or at the start of processing of the workflow.

2. The method as claimed in claim 1, further comprising:
  automatically identifying a recurring usage scheme of a client user in the stored usage and status data via the analysis module;
  automatically generating, by the analysis module, a usage scheme that automatically executes a command sequence identified within the stored usage and status data; and
  automatically storing, by the analysis module, the generated usage scheme in the default settings of the application.

3. The method as claimed in claim 2, further comprising:
  identifying, through the analysis of the stored usage and status data and via the analysis module, which processing routines a client user regularly executes in a segment of a user interface of the application or when a workflow is performed by way of the associated application frontend module; and modifying the default settings of the application via the analysis module such that the identified processing routines are automatically executed in the segment or when the workflow is performed.

4. The method as claimed in claim 2, further comprising: determining, through the analysis of the stored usage and status data and via the analysis module, the frequency with which control elements of a user interface of the application are actuated; and
modifying the default settings of the application via the analysis module such that the control elements are arranged on the user interface in accordance with the actuation frequency.

5. The method as claimed in claim 2, further comprising: determining, via the analysis module, the frequency with which specific datasets; and
allocating a storage location, determined in accordance with the access frequency, to said datasets.

6. The method as claimed in claim 2, further comprising: determining, via the analysis module, the frequency with which the application is invoked; and
causing, if said determined call frequency exceeds a threshold value, the analysis module to start an application backend module of the application independently of an associated application frontend module.

7. The method as claimed in claim 2, further comprising: determining, via the analysis module, the consumption of resources by the application of the client-server system; and
starting the application, in the case of a client-side call, via an application starter only if sufficient free resources are available on the client-server system.

8. The method as claimed in claim 2, wherein the usage and status data stored in the database is analyzed discontinuously by way of the analysis module at regular time intervals, in particular once per day; and
the usage and status data acquired by way of the monitoring frontend module includes details concerning at least one of:
the identity of a client user,
the or each application invoked by the client user, the attributes of the used layout of the application,
the status of a user interface of the application,
the data loaded by the application, the user commands directed to the application, and the start time of the interaction.

9. The method as claimed in claim 1, further comprising: determining, through the analysis of the stored usage and status data and via the analysis module, the frequency with which control elements of a user interface of the application are actuated; and
modifying the default settings of the application via the analysis module such that the control elements are arranged on the user interface based on the actuation frequency.

10. The method as claimed in claim 1, further comprising: determining, via the analysis module, the frequency with which specific datasets are accessed by way of the application; and
allocating a storage location to said datasets based on the access frequency.

11. The method as claimed in claim 1, further comprising: determining, via the analysis module, the frequency with which the application is invoked; and
causing the analysis module to start an application backend module of the application independently of an associated application frontend module, if said determined call frequency exceeds a threshold value.

12. The method as claimed in claim 1, further comprising: determining, via the analysis module, the consumption of resources by the application of the client-server system; and
starting the application, in the case of a client-side call, via an application starter only, if sufficient free resources are available on the client-server system.

13. The method as claimed in claim 1, wherein the usage and status data stored in the database is analyzed discontinuously by way of the analysis module at regular time intervals, in particular once per day.

14. The method as claimed in claim 13, wherein the usage and status data stored in the database is analyzed discontinuously by way of the analysis module once per day.

15. The method as claimed in claim 1, wherein usage and status data acquired by way of the monitoring frontend module includes details concerning at least one of:
the identity of a client user,
the or each application invoked by the client user,
the attributes of the used layout of the application,
the status of a user interface of the application,
the data loaded by the application,
the user commands directed to the application, and the start time of the interaction.

16. A client-server system for automatically improving performance of a software application, the system comprising:
a monitoring frontend module implemented by executing instructions from memory on a processor associated with a client side of the client-server system;
a monitoring backend module implemented by executing instructions from memory on a processor associated with a server side of the client-server system,
the monitoring frontend module configured to,
continuously acquire data relating to usage and operating status of a frontend module of the application implemented on the client side during the execution of the application, and
transmit said acquired usage and status data to the monitoring backend module, and
the monitoring backend module configured to store the usage and status data in a database on the server side; and
an analysis module configured to,
automatically analyze the usage and status data stored in the database,
identify, based on the analysis of the stored usage and status data, that segment of a user interface including a plurality of segments with which a client user will first interact on via client side after starting the application frontend module, and
automatically modify default settings of the application on the basis of a result of the analysis in order to improve performance of the application, the default settings indicating the segment of the user interface that are frequently first used by the user after starting the application such that the identified segment is automatically placed in a foreground of the user interface when the application frontend module is started or at the start of processing of the workflow.

17. A non-transitory computer readable medium including program segments for, when executed on a computer device, causing the computer device to implement the method of claim 1.

* * * * *